United States Patent [19]

Bogart

[11] Patent Number: 4,874,693
[45] Date of Patent: Oct. 17, 1989

[54] METHOD FOR ASSESSING PLACENTAL DYSFUNCTION

[76] Inventor: Mark Bogart, 3432 Pershing Ave., San Diego, Calif. 92104

[21] Appl. No.: 917,985

[22] Filed: Oct. 10, 1986

[51] Int. Cl.$^4$ .................. G01N 33/53; G01N 33/543; G01N 33/577; C12Q 1/68
[52] U.S. Cl. .......................................... 435/7; 435/6; 436/518; 436/544; 436/548; 436/814; 436/818
[58] Field of Search ............... 435/7, 6; 436/548, 500, 436/506, 544, 65, 814, 817, 818, 518

[56] References Cited

U.S. PATENT DOCUMENTS

| | | | |
|---|---|---|---|
| 4,474,893 | 10/1984 | Reading | 436/548 |
| 4,496,658 | 1/1985 | Kondo et al. | 436/814 |
| 4,514,505 | 4/1985 | Canfield et al. | 436/500 |
| 4,560,649 | 12/1985 | Saxena et al. | 436/817 |

OTHER PUBLICATIONS

Chemical Abstract, Crosignani, vol. 75, 1971, No. 107674y.
Chemical Abstract, Gaspard et al., vol. 102, 1985, No. 143209k.
Pandian et al., Clin. Chem., vol. 31, 1985.
Arnholdt et al., Geburtshilfe Frauenheilkd, 44(5), May 1984, pp. 328–332.
Vassilakos et al., *Am. J. Obstet. Gynecol.*, 127, 2, 167, (1977).
Göcke et al., *Verh. Dt. Ges. Path.*, 66, 141, (1982).
Wald et al., *Brit. Med. J.*, 297, 6653, 883, (1988).
Bharathur et al., *Am. J. Human Genetics*, 43, 3, A226, (1988), No. 0901.
Arab et al., *Am. J. Human Genetics* 43, 3, A225, (1988), [No. 0896].
Lustig et al., *Am. J. Med. Genetics*, 31, 211, (1988).

*Primary Examiner*—Esther M. Kepplinger
*Assistant Examiner*—Florina B. Hoffer
*Attorney, Agent, or Firm*—Brown, Martin, Haller & McClain

[57] ABSTRACT

A method is presented for detecting placental dysfunction that is diagnostic of aneuploid chromsomal abnormalities. It is particularly useful for diagnosing pregnancies at risk for fetal aneuploid chromosome abnormalities, and consists of quantitating the hormone human chroionic gonadotropin (HCG) alone or in combination with the free alpha subunit of HCG (alpha-HCG). In a preferred embodiment of the invention, bodily fluids from women between 18 and 25 weeks of gestation are assayed using an immunoassay. Levels of 2.5 or more multiples of the median value for normal pregnancies (MOM) for HCG and/or alpha-HCG are indicative of fetal chromosome abnormalities. This test will detect approximately 70% of fetuses with chromosome aneuploidy.

17 Claims, 3 Drawing Sheets

METHOD FOR ASSESSING PLACENTAL DYSFUNCTION

BACKGROUND OF INVENTION

A major cause of birth defects is due to chromosome abnormalities, particularly aneuploidy. An increased incidence of aneuploid babies born to women over 35 years of age was first identified by Penrose in 1933 and now forms the basis for genetic counseling in prenatal diagnosis. While the risk for chromosomal disorder in the liveborn offspring of women ages 35 and older ranges from 1.21% at age 35 to 8.12% at age 46, the contribution of these older mothers to the total incidence of chromosomally abnormal babies is only about 25%, due to the vastly larger numbers of babies born to women under 35 years of age. This means that currently by performing amniocentisis on the approximately 6% of pregnant women who are 35 or older, 25% of chromosomally abnormal fetuses can be detected. Conversly, this also means that about 75% of chromosomally abnormal features are born to the younger age group of women who are not offered genetic amniocentisis.

While using maternal age as a screening parameter is clearly useful, other parameters or tests are needed, particularly biochemical tests which can be offered to pregnant women regardless of age. In this regard Merkatz et al have shown that low levels of maternal serum alphafetoprotein (AFP) are somewhat correlative wit fetal chromosome abnormalities. However, this test appears to have limited wide spread applicability since recent studies have shown that in pregnant women with low AFP levels only about 20% actually carried a chromosomally abnormal fetus.

SUMMARY OF INVENTION

An assay is described for detecting placental dysfunction that is indicative of chromosomally abnormal fetuses, having a success rate of up to about 80% and premised on measuring maternal levels of human chorionic gonadotropin hormone (HCG) or HCG and the free alpha subunit of HCG (alpha-HCG). The assay consists of measuring the levels of HCG or HCG and alpha-HCG in the bodily fluids of pregnant women using immunoassay techniques. A wide variety of immunochemical assays can be employed including competitive and noncompetitive binding assays, performed in solution or on solid surfaces. Particularly useful assay reagents are antibodies that recognize epitopes on the beta subunit of the alpha subunit of HCG.

The assay is particularly diagnostic of fetal chromosome abnormalities when performed on females that are between 18 and 25 weeks gestation. The assay has a low false positive rate of about 1% when an elevated level of HCG alone or HCG and alph-HCG is the indicator of fetal abnormality. Levels of HCG and/or alpha-HCG of 2.5 or more multiples of the median values for normal pregnancies (MOM) are indicative of fetal chromosome abnormality. Additional features of the subject invention are that the assay indicates chromosome abnormality independent of the age of the mother. Because this assay evaluates HCG which is primarily produced by the fetal placenta, any abnormality that affects the production or control of production of HCG may be detected. In essence, this assay evaluates placental function and is, therefore, not limited to only detecting chromosomally abnormal fetuses.

DETAILED DESCRIPTION OF INVENTION

Figure 1:
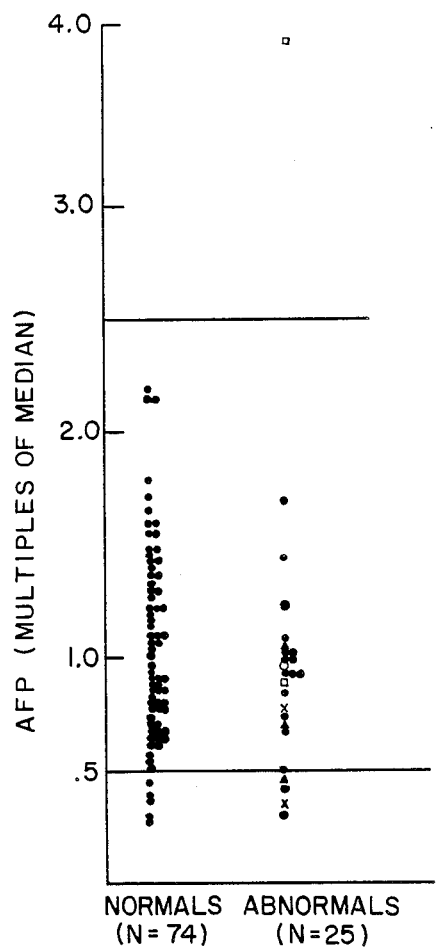
FIG. 1 presents a graphic profile of AFP for patients carrying normal and chromosomally abnormal fetuses.
(●=trisomy 21; □=trisomy 13; ▲=trisomy 18; X=XO and XO/XY mosaics; o=10 q+)

The subject invention assay pesents a method for assessing plcental function that is useful for detecting chromosomal abnormalities in fetuses carried by women that are approximately 18 to 25 weeks of gestation. The assay is premised on detecting elevated levels of HCG and/or alpha-HCG. In the preferred embodiment of the invention, these molecules are detected and quantitated using antibodies that recognize specific epitopes present on the beta and on the alpha chains of HCG. The assay is maximally reliable when it is conducted on bodily fluids taken from women that are between 18 and 25 weeks of gestation. This is because in normal pregnancies HCG levels fluctuate dramatically prior to 18 weeks, but remain stable from 18–25 weeks. The subject invention assay relies on detecting abnormal levels (particularly, but not exclusively, elevated levels) of HCG and/or alpha-HCG rather than on just the presence or absence of HCG and/or alpha-HCG. Therefore, values from normal pregnancies need to be accounted for when determining if a women has an abnormal hormone level. Thus, this is most readily done between 18–25 weeks of gestation.

It is well known that different types of immunoassays, and even the same type assay performed in different laboratories, give different results in terms of absolute quantities of a particular hormone measured. The use of multiples of the median value for normal pregnancies (MOM) to determine which patients have abnormal levels is a convenient (but not the only) method to account for the variation in hormone measurements. By using MOM, various assay methods and procedures can be used to produce the same diagnostic result even if the absolute quantities of a hormone measured differ with differing immunoassay techniques. It will be appreciated that the subject assay may also be useful for detecting fetal chromosome abnormalities earlier than 18 weeks of gestation provided techniques such as MOM calculations are used to account for normal hormone levels for each week of gestational age.

While it is anticipated that HCG and alpha HCG will be primarily assayed in serum or urine of pregnant women, there is in fact no reason for limiting the assay to these two types of bodily fluids. It is known that HCG and alpha-HCG are found in tears and other bodily fluids, and that the levels of these molecules increase in these fluids during pregnancy as they do in urine and serum. Consequently, the subject assay can be conducted on virtually any bodily fluid that contains HCG and/or alpha-HCG.

The assay described herein is an immunoassay that utilizes antibodies that bind to epitopes on the beta and alpha subunits of HCG that are used to detect the quantities of HCG and free alpha-HCG. We have found that levels of HCG equal to or greater than 2.5 MOM (17 IU/ml) are detected in 56% of pregnant women with chromosomally abnormal fetuses. Additionally, we have found that elevated levels of the free alpha subunit of HCG allow detection of an additional 12% of chromosomally abnormal fetuses. Thus, by measuring both HCG and alpha-HCG approximately 70% of women with chromosomally abnormal fetuses can be detected with a false positive rate of only about 1%. It should also be noted that very low levels of HCG (less than 0.25 MOM) were observed in 8% of women with chromosomally abnormal fetuses. Therefore, using both elevated and low levels of HCG and/or alpha-HCG, up to nearly 80% of chromosomally abnormal fetuses can be detected with a total false positive rate of about 4%. Comparative testing with the only other biochemical indicator of chromosomal defects, alpha fetoprotein (AFP), shows that AFP only detects about 25% of those women that carry a chromosomally abnormal fetuses with a false positive rate of about 6%.

In performing the immunochemical assay for either HCG, or HCG and alpha HCG, bodily fluids containing these molecules and antibodies to either one or both will be employed in forming a detectable "immunocomplex". While the exact physical nature of the complex is not fully known, its formation, nonetheless makes possible the subject assay. Formation of an immunocomplex can be achieved in many ways. For example, it is to be anticipated that a competitive equilibrium assay can be utilized where all the reactants are in solution, or where at least one of the antibodies is attached to a solid surface.

In the solution competitive equilibrium assay situation, where the sample contains the antigens and antibodies to HCG and alpha-HCG, bodily fluids containing these molecules and antibodies to either one or both will be employed in forming a detectable "immunocomplex".

Formation of an immunocomplex can be achieved in many ways. For example it is to be anticipated that a competitive equilibrium assay can be utilized where all the reactants are in solution, or where at least one of the antibodies is attached to a solid surface. In the solution competitive equilibrium assay situation, the sample containing the antigens and antibodies to HCG, alpha-HCG or both of these molecules are brought together in an aqueous medium, normally having a pH of about 6-9.

Tracer amounts of labeled antigens are added to the sample to complete for binding to their respective antibodies with HCG and/or alpha HCG present in the sample. Partitioning on labeled HCG and/or alpha-HCG occurs via being bound and unbound to antibody. Bound labeled amounts of these molecules may then be separated from their unbound counterparts, and the amount of HCG and/or alpha-HCG determined in accordance with the nature of the label, by comparison to control samples similarly treated and containing known amounts of these molecules.

In the above types of assays, all the materials can be brought together simultaneously, or the sample can be combined with the requisite antibodies followed by the addition of labeled HCG, and/or alpha-HCG. Further incubation steps may be involved between the various additions usually not being less than 5 minutes or more than about 24 hours. Additionally, either a rate or equilibrium measurement may be involved.

The second class of immunoassays that are anticipated to be employable in the subject invention are referred to as "2-site" or "sandwich" assays. Here, a fluid sample from a pregnant women is incubated with an excess of antibody bound to at least one solid surface and directed against HCG, and/or alpha-HCG. Subsequently, labeled second antibodies, also in excess but directed against a second determinant on HCG and/or alpha-HCG are incubated with the immunocomplex formed with the first antibody attached to the solid substrate. The presence of the labeled second antibodies on the surface of the immunocomplex can then be determined by suitable means depending on the type of label used. A variety of "sandwich assay" are described in the prior art, and they are hereby incorporated by reference. Particularly useful are assays shown in U.S. Pat. No. 4,376,110 and U.S. Pat. No. 4,244,940.

It will be apparent to those skilled in the art that a two site assay is particularly effective for determining HCG and/or alpha HCG. For example, an antibody (monoclonal or polyclonal) specific to the beta chain of HCG can be attached to the solid surface which in turn will bind intact HCG. Subsequently, a labeled second antibody, again mono or polyclonal, directed against the alpha subunit of HCG can be employed to bind the alpha chain, and thereby indicate the presence of the immunocomplex on the solid substrate. It will be appreciated that the assay is also workable if antibody against the alpha subunit of HCG is affixed to the solid substrate and the labeled second antibody binds to the beta subunit of HCG.

In order to assay free alpha-HCG in a sample containing HCG, antibodies that do not recognize alpha HCG in combination with the beta subunit should be utilized. One such antibody exists and has been described by Pandian et al, *Clin. Chem.* 31, 980 (1985). Other monoclonal antibodies having unique alpha-HCG binding capacity can be generated by the hybridoma techniques well known to those skilled in the art.

Depending on the type of immunoassay utilized in the present invention, various labels to monitor the presence of either HCG and/or alpha-HCG or antibodies directed to either of these molecules may be employed. The choice of label will be dictated in part by the sensitivity of the material being assayed, as well as cost and availability of reagents.

A variety of labels are well known and routinely used in immunoassays such as radionuclides (particularly $I^{125}$), enzymes, fluorescers, magnetic particles, stable free radicals, etc. Prior art illustrative of these labels are U.S. Pat. Nos. 3,654,090; 3,867,517; 3,996,345 and 4,020,151.

There are routinely used in immunoassays a variety of fluorescers including fluorescein, densyl, rhodamines, acradines, etc. Suitable enzymes employable in this invention include beta-galactosidase, alkaline phosphatase and horseradish peroxidase, as well as others well known to those skilled in the art.

As allued to above, a variety of radionuclides are employable as suitable levels. Moreover, the procedures for attaching or metabolically labeling proteins with these labels are well known. For instance, radiolabeling proteins with iodine can be achieved by the lactoperoxidase method well known to those skilled in the art, or may involve indirect binding using the Bolton-Hunter or similar reagent.

Assaying for either HCG and/or alpha-HCG can be effected using antibodies that are polyclonal or monoclonal. The former are generated using HCG, the beta subunit of HCG or alpha-HCG, and injecting these molecules into an animal to effect an immune response, thereby resulting in the reproduction of antibodies. Suitable animals are sheep, goats, mice, rats and rabbits, though other animals may also be used. Polyclonal antibody can be prepared from crude sera by absorption or salt precipitation techniques to yield highly specific antibodies. These techniques are well known to those skilled in the art. It should be noted that both polyclonal and monoclonal antibodies to HCG are commercially available.

In addition to preparing polyclonal antibodies, it is well known that monoclonal antibodies can be generated that are useful in a variety of immunochemical assays, particularly "two-site" assays. The procedure for generating monoclonal antibodies is described by Kohler and Milstein, *Nature*, 356, 495–597 (1975). Kohler and Milstein primarily show the preparation of monoclonal antibodies of mouse origin. In addition, monoclonal antibodies of human origin can be prepared as described by Glassy et al in *Monoclonal Antibodies in Cancer*, (Boss et al, eds.; Academic Press: (1983)) and Glassy et al, *National Academy of Sciences, U.S.A.*, 80, 6237 (1983). The method of Heitzmann and Cohn described in *Molecular Biology and Medicine*, 1, 235, 243 (1983) may also be utilized to generate monoclonal antibodies against HCG or alpha-HCG.

If a two site solid phase immunoassay is employed in the subject assay invention, attachment of antibody to the solid substrate may be by procedures known to those skilled in the art, such as absorption or by covalent binding directly or through chemical linkers of sorts also well known to those skilled in the art. Simple methods for carrying out these procedures are given, for example, by Iman and Hornby in *Biochemical Journal*, 129, 255–259 (1972) and Campbell, Hornby & Morris in *Biochemical Biophysical Acta*, 397, 384–392 (1985). Also it should be noted that solid surfaces chemically pretreated and suitable for binding antibody can be purchased commercially.

A preferred embodiment of the subject invention will involve secondary antibodies carrying a label wherein the label is capable of effecting a color change indicative of the presence of HCG and/or alpha-HCG. Generally this will involve a label comprising an enzyme molecule that hydrolyzes a colorless substrate to produce a detectable color change of the solution bathing the solid surface, or a change in the color of the solid surface. In either instance, the degree of color can be monitored to indicate the levels of HCG and/or alpha-HCG.

Particularly useful two site assays are those in which two solid surfaces are used to assay HCG and/or alpha-HCG. By attaching the appropriate antibodies to two separate sites on one or more surfaces simultaneous assay of both HCG and alpha-HCG may be accomplished using a single aliquot of fluid.

A wide variety of enzymes are suitable for attachment to antibody. For example, horseradish peroxidase can be employed, as well as beta-galactosidase, glucose oxidase, alkaline phosphatase, etc. These enzymes utilize primarily tetrazolium salts well known to those skilled in the art as substrate. The procedures for generating horseradish peroxidase antibody conjugates and purifying the same are described by Arendo in *Methods of Enzymology*, 73, 166–173 (1981).

The following examples are for illustrative purposes and are not intended to be a delineation of all ways by which HCG and/or alpha-HCG can be assayed.

EXAMPLE 1

Alpha-fetoprotein (AFP) and HCG Levels in Maternal Serum

HCG levels were measured in women carrying chromosomally normal and abnormal fetuses. A total of 74 women carrying normal fetuses and 25 women carrying chromosomally abnormal fetuses were studied. Table 1 below shows the type of chromosomal abnormalities of the 25 abnormal fetuses. Table 2 below presents the AFP levels measured and the gestational age when the samples were obtained from the various mothers carrying chromosomally abnormal fetuses. Also shown in Table 2 are the levels of HCG and alpha-HCG. These data are presented in graphic form in FIGS. 1, 2 and 3.

TABLE 1

| ABNORMALITY | NUMBER OF CASES |
|---|---|
| Trisomy 21 | 17 |
| Trisomy 18 | 3 |
| Trisomy 13 | 2 |
| Monosomy X | 1 |
| Mosaic XO/XY | 1 |
| 46,XY,10q+ | 1 |
| | 25 |

TABLE 2

| Case # | Gestation (Weeks) | AFP (ng/ml) | (MOM) | hCG (IU/ml) | (MOM) | Alpha-hCG (ng/ml) | (MOM) | Ab |
|---|---|---|---|---|---|---|---|---|
| 935 | 18 | 44.0 | (1.05) | 26.7 | (3.22) | 230 | (1.43) | +21 |
| 912 | 20 | 30.8 | (0.50) | 39.8 | (4.80) | 370 | (2.31) | +21 |
| 989 | 20 | 239.2 | (3.93) | 34.5 | (4.15) | 410 | (2.56) | +13 |
| 193 | 19 | 41.0 | (0.94) | 13.8 | (1.66) | 330 | (2.06) | +21 |
| 871 | 18 | 44.0 | (1.05) | 32.6 | (3.93) | 380 | (2.38) | +21 |
| 581 | 19 | 39.0 | (0.89) | 11.2 | (1.35) | 170 | (1.06) | +13 |
| 736 | 20 | 21.4 | (0.35) | 39.8 | (4.80) | 280 | (1.75) | XO |
| 758 | 19 | 31.4 | (0.72) | 23.8 | (2.87) | 330 | (2.06) | +21 |
| 8360 | 19 | 45.0 | (1.03) | 36.8 | (4.43) | 370 | (2.31) | +21 |
| 8727 | 18 | 45.0 | (1.07) | 14.6 | (1.76) | 290 | (1.81) | +21 |
| 8594 | 22 | 85.0 | (1.04) | 9.2 | (1.11) | 430 | (2.69) | +21 |
| 9127 | 21 | 87.2 | (1.21) | 14.9 | (1.80) | 460 | (2.88) | +21 |
| 8908 | 25 | 169.8 | (1.68) | 23.0 | (2.77) | 460 | (2.88) | +21 |
| 7445 | 20 | 65.4 | (1.07) | 1.1 | (0.13) | 280 | (1.75) | +18 |
| 7958 | 19 | 32.2 | (0.73) | 0.7 | (0.08) | 120 | (0.75) | +18 |

TABLE 2-continued

| Case # | Gestation (Weeks) | AFP (ng/ml) | (MOM) | hCG (IU/ml) | (MOM) | Alpha-hCG (ng/ml) | (MOM) | Ab |
|---|---|---|---|---|---|---|---|---|
| 7775 | 21 | 30.4 | (0.42) | 33.6 | (4.05) | 370 | (2.31) | +21 |
| 8848 | 22 | 63.2 | (0.77) | 10.5 | (1.27) | 300 | (1.88) | XO/XY |
| 7497 | 19 | 62.4 | (1.43) | 39.2 | (4.72) | 590 | (3.69) | +21 |
| 9388 | 21 | 65.8 | (0.93) | 63.2 | (7.61) | 400 | (2.50) | +21 |
| 8365 | 20 | 42.6 | (0.70) | 12.2 | (1.47) | 400 | (2.50) | +21 |
| 489 | 21 | 60.8 | (0.84) | 22.9 | (2.76) | 340 | (2.13) | +21 |
| 12 | 20 | 57.2 | (0.94) | 15.4 | (1.86) | 200 | (1.25) | +21 |
| 488 | 19 | 20.0 | (0.46) | 53.8 | (6.48) | 270 | (1.69) | +18 |
| 8423 | 21 | 71.4 | (0.99) | 17.9 | (2.16) | 300 | (1.88) | 10q+ |
| 1255 | 21 | 20.8 | (0.29) | 22.5 | (2.71) | 320 | (2.00) | +21 |

The data were gathered using the method of Ruoslahti et al, described in *Natl. Canc. Inst.*, 49, 623-650 (1972) for measuring AFP using a radioimmunoassay. Modifications in the published procedure include separating bound AFP from free AFP using goat anti-rabbit gamma globulin as the second antibody. Highly purified AFP was used as the standard and was calibrated against the Center for Disease Control AFP standard. The intra-assay varition was 9.4% and the interassay variation was 11.2%.

The assay employed to detect and quantitate HCG was that of Pandian et al., *Endocrinology*, 107, 1564-1571 (1980), also described above. This is a radioimmunoassay and utilizes an antibody that recognizes HCG by binding to an epitope on the beta chain of the molecule. The antibody exhibits little or no cross activity with alpha-HCG, lutenizing hormone, follicle stimulating hormone, or thyrotropin. HCG standard was calibrated against the World Health Organization, Second International Reference preparation. The intra-assay variation was 6.2% and the inter-assay variation was 7.8%. Samples were routinely assayed over a range of dilutions including 1:10, 1:100, 1:1000.

Because maternal serum AFP levels rise with increasing age, it is necessary to obtain a median value for each gestational age for women carrying normal fetuses, to be able to compare this value to AFP levels associated with chromosomally abnormal fetuses. However, because HCG levels do not fluctuate over the gestation period tested (18-25 weeks), HCG levels determined in pregnant women were compared to a single median value derived from maternal serum of women carrying normal fetuses.

FIG. 1 shows the relationship of AFP levels and fetal chromosomal normality or abnormality. FIG. 1 also shows that there were 5 chromosomally abnormal fetuses with AfP levels of 0.5 MOM or less, and one with an AFP level higher than 2.5 MOM. Thus, out of 25 fetuses that were confirmed as being chromosomally abnormal, only 6 (24%) displayed abnormal levels of AFP.

Figure 2:
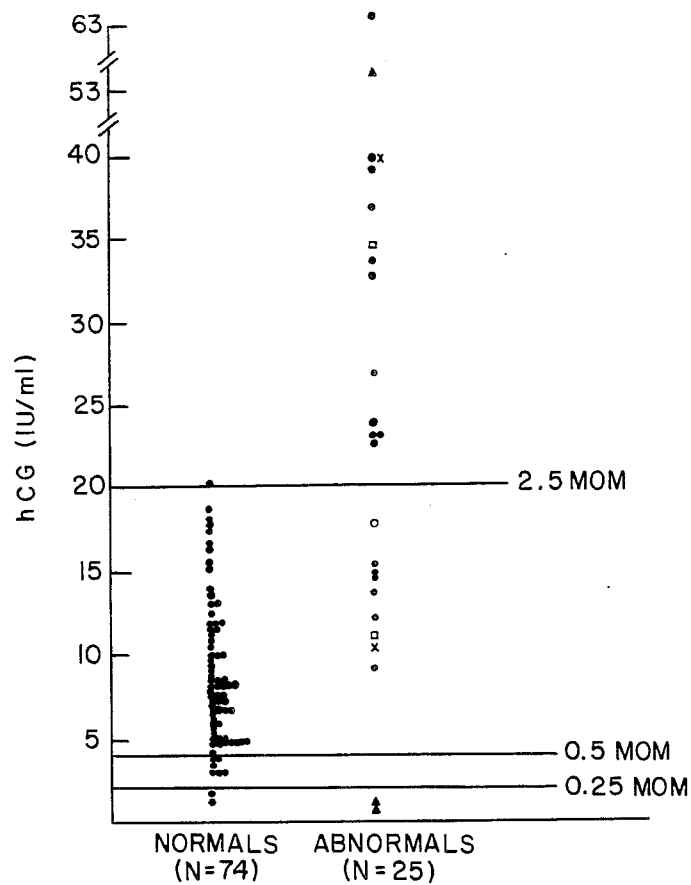
FIG. 2 shows HCG levels expressed as international units/per milliliter from patients carrying both normal and chromosomally abnormal fetuses. MOM stands for "multiples of the median".
(●=trisomy 21; □=trisomy 13; ▲=trisomy 18; X=XO and XO/XY mosaics; o=10 q+)

FIG. 2 shows the relationship of maternal serum HCG levels with fetal chromosomal normality or abnormality. The median HCG value for the 74 women carrying normal fetuses during the gestation period of 18-25 weeks was 8.0 International Units/per milliliter. The most interesting feature of FIG. 2 is that it shows 14 serum samples from women carrying chromosomally abnormal features having HCG levels greater than 2.5 MOM, while only 1 serum sample from a women carrying a chromosomally normal fetus had a value greater than 2.5 MOM.

It should also be noted that 2 of 25 samples from women with chromosomally abnormal fetuses had HCG levels less than 0.25 MOM, as did 2 of 74 samples from women with chromosomally normal fetuses.

From a comparative standpoint, it is easily seen that abnormal levels of HCG, particularly elevated levels, are more predictive of having a chromosomally abnormal fetus than are low serum AFP levels.

EXAMPLE 2

Measurement of Alpha-HCG and Relationship to Chromosomally Abnormalities

The materials and methods described in this Example are similar to those described in Example 1 with the exception that alpha-HCG was assayed. A radioimmunoassay procedure was utilized, as described above by Pandian et al, (1985). A serum sample from each of the cases shown in Table 2 was incubated with a monoclonal antibody (A 109) that recognizes alpha-HCG. $I^{125}$ labeled alpha-HCG was utilized to compete with alpha-HCG present in the sample. The assay is specific for alpha-HCG and exhibits no cross reactivity with the beta subunit of HCG, luteinizing hormone, follicle stimulating hormones, or thyrotropin hormone. However, because it does exhibit a slight crossreactivity (2.4% on a molar basis) with HCG, additional accuracy is realized by correcting for this cross reactivity. It was determined that the assay has an intra-assay variation of 5.1% and an inter-assay variation of about 6.0%.

Figure 3:
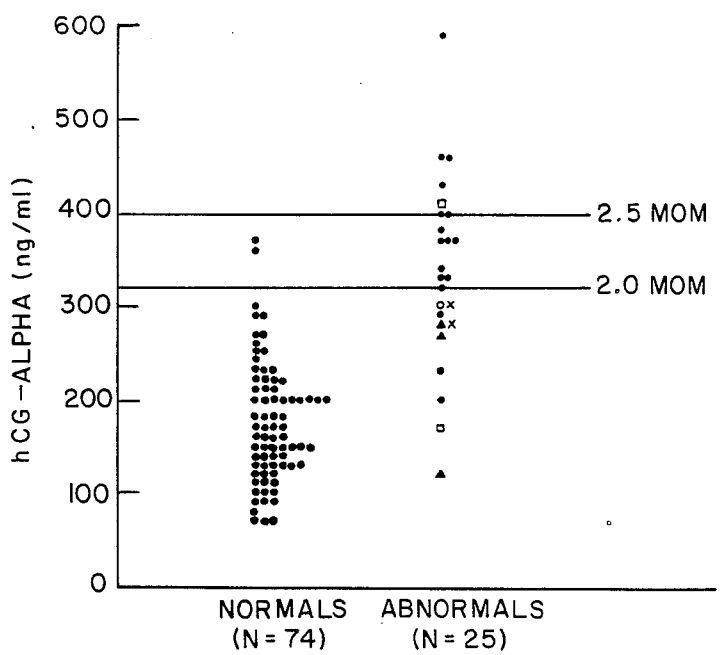
FIG. 3 presents alpha-HCG levels present in maternal serum from patients carrying normal and chromosomally abnormal fetuses. MOM stand for multiples of the median.
(●=trisomy 21; □=trisomy 13; ▲=trisomy 18; X=XO and XO/XY mosaics; o=10 q+)

Using the Pandian et al (1985) procedure described above, it was shown that alpha-HCG levels are increased in maternal serum from some females carrying chromosomally abnormal fetuses. FIG. 3 presents the results obtained for 74 women carrying normal fetuses that were 18-24 weeks pregnant, and for 25 women that carried chromosomally abnormal fetuses. It can be seen that the median normal alpha-HCG level is about 160 ng/ml. Further, it is apparent that none of the women carrying normal fetuses had an alpha-HCG level equal to or greater than 2.5 MOM. In contrast, 28% of females carrying abnormal fetuses had an alpha-HCG level equal to or greater than 2.5 MOM. It is important to note that of the 7 patients that displayed elevated alpha-HCG levels, 4 of these also exhibited elevated HCG levels. These are cases 989, 8908, 7497 and 9388 shown in Table 2. Three females that presented elevated alpha-HCG had normal levels of HCG. These are cases 8954, 9127 and 8365 shown in Table 2.

EXAMPLE 3

Simultaneous Detection of HCG and Alpha-HCG

The materials and methods described in this example are similar to those in the proceeding examples with the following exceptions. A monoclonal antibody can be attached to a solid surface that recognizes an epitope on alpha-HCG which is available for antibody binding only when alpha-HCG is physically separated from the beta chain of HCG. In addition, a second monoclonal antibody specific to an epitope on the beta chainn of HCG is bound to a separate region on the solid surface. Subsequently, these solid surfaces are immersed in assay sample fluid containing either unknown or known amounts of HCG and alpha-HCG. The assay is run on a sample containing known amounts of HCG and alpha-HCG to obtain data from which to construct a standard curve.

After a period of incubation to permit saturation binding of HCG and alpha-HCG to their respective antibodies, the solid surfaces are washed with a suitable physiological buffer to remove any unbound reactants, and then labeled second antibody is added. The latter can be a monoclonal antibody that recognizes a common epitope on the alpha chain that is bound to the beta chain, and the alpha chain which is not bound to the beta chain. In this instance, the monoclonal antibody can have associated with it an enzyme label capable of yielding a color reaction in the presence of a suitable substrate. Thus, second antibody can be labeled with alkaline phosphatase, beta-galactosidase, or like enzyme.

After an incubation period sufficent to realize discernable color, the reaction can be stopped with either acid or base, and the amount of color present correlated with amounts indicative of HCG and alpha-HCG concentration. The amount of color present can be quantitated using known special photometric techniques.

It will be understood that although the foregoing invention has been described by way of illustration and example, that this is for clarity of understanding, and that there exists a variety of imaginable changes and modifications that may be practiced within the appended claims.

We claim:

1. A method for identifying a pregnant women with substantial risk of gestating a fetus having an aneuploid chromosomal abnormality, comprising
   a. combining bodily fluids taken from said female gestating said fetus during the 18th through 25th weeks of her pregnancy in an aqueous buffered assay medium with labeled human chorionic gonadotropin (HCG) hormone, wherein said label provides a detectable signal and antibodies to HCG;
   b. determining the amount of labeled HCG either bound or unbound to said antibodies as a measure of HCG in said sample; and
   c. comparing the level of said HCG in said sample with levels of HCG measured during the same time interval of pregnancy in women gestating normal fetuses, said comparison being determinative of the presence of the aneuploid abnormality in said fetus.

2. A method according to claim 1 wherein said label is radioactive.

3. A method according to claim 1 wherein said label is an enzyme.

4. A method for identifying a pregnant women with substantial risk of gestating a fetus having an aneuploid chromosomal abnormality, comprising
   a. combining bodily fluids taken from said female gestating said fetus during the 18th through 25th weeks of her pregnancy in an aqueous buffered assay medium with labeled human chorionic gonadotropin (HCG) hormone and labeled alpha-human chorionic gonadotropin (alpha-HCG) hormone, wherei said label provides a detectable signal and antibodies to HCG and alpha-HCG;
   b. determining the amount of labeled HCG and labeled alpha-HCG either bound or unbound to said antibodies as a measure of HCG and alpha-HCG in said sample; and
   c. comparing the level of said HCG and alpha-HCG in said sample with levels of HCG and alpha-HCG measured during the same time interval of pregnancy in women gestating normal fetuses, said comparison being determinative of the presence of the aneuploid abnormality in said fetus.

5. A method according to claim 4 wherein said label is radioactive.

6. A method according to claim 5 wherein said label is an enzyme.

7. A method for diagnosing placental dysfunction indicative of fetal aneuploid chromosomal abnormalities comprising quantifying elevated levels of human chorionic gonadotropin hormone or its subunits in a bodily fluid taken from the women gestating said fetus during the 18th through 25th weeks of her pregnancy, by:
   a. contacting one or more first antibody molecules correspondingly reactive with said gonadotropin hormone or its subunits and which antibodies are attached to one or more solid surfaces with the body fluid to form primary complexes on the solid surfaces, and isolating said primary complexes;
   b. contacting said primary complexes with one or more labeled second antibody molecules correspondingly reactive with said gonadotropin hormone or its subunits to form secondary complexes on said one or more solid surfaces, and isolating said second complexes; and
   c. comparing the amount of labeled second antibody molecules correspondingly reactive with said gonadotropin hormone or its subunits with amounts of labeled antibody measured for control samples prepared in accordance with steps a and b and taken from women gestating normal fetuses during the same time interval of their pregnancies, said comparison being correlated with the level of gonadotropin hormone or its subunits in said female and determinative of the presence of the aneuploid abnormality in said fetus.

8. A method as described in claim 7 wherein said gonadotropins and/or its subunits are selected from the group consisting of HCG, alpha-HCG, and beta-HCG.

9. A method as described in claim 8 wherein said labeled second antibody molecules comprise enzymes capable of producing a color signal indicative of said gonadotropins and/or its subunits when combined with substrate.

10. A method as described in claim 8 wherein said one or more second antibody molecules correspondingly reactive with said gonadotropins and/or its subunits comprises antibodies selected from the group consisting of polyclonal and monoclonal antibodies.

11. A method for identifying a pregnant women with substantial risk of gestating a fetus having an aneuploid chromosomal abnormality, comprising:
   a. combining bodily fluids taken from said female gestating said fetus during the 18th through 25th weeks of her pregnancy in an aqueous buffered assay medium with labeled alpha-human chorionic gonadotropin (alpha-HCG) hormone, wherein said label provides a detectable signal and antibodies to alpha-HCG;

b. determining the amount of labeled alpha-HCG either bound or unbound to said antibodies as a measure of alpha-HCG in said sample; and c. comparing the level of said alpha-HCG in said sample with levels of alpha-HCG measured during the same time interval of pregnancy in women gestating normal fetuses, said comparison being determinative of the presence of the aneuploid abnormality in said fetus.

12. A method according to claim 11 wherein said label is an enzyme.

13. A method according to claim 12 wherein said label is radioactive.

14. A method as described in claim 1 wherein said chromosomal abnormality is selected from the group consisting of trisomy 21, trisomy 18, trisomy 13, monosomy X, mosaic XO/XY and 46 XY, 10 q+.

15. A method as described in claim 4 wherein said chromosomal abnormality is selected from the groups consisting of trisomy 21, trisomy 18, trisomy 13, monosomy X, mosaic XO/XY and 46 XY, 10 q+.

16. A method as described in claim 7 wherein said chromosomal abnormality is selected from the groups consisting of trisomy 21, trisomy 18, trisomy 13, monosomy X, mosaic XO/XY and 46 XY, 10 q+.

17. A method as described in claim 11 wherein said chromosomal abnormality is selected from the groups consisting of trisomy 21, trisomy 18, trisomy 13, monosomy X, mosaic XO/XY and 46 XY, 10 q+.

* * * * *

UNITED STATES PATENT AND TRADEMARK OFFICE
CERTIFICATE OF CORRECTION

PATENT NO. : 4,874,693
DATED : October 17, 1989
INVENTOR(S) : Mark Bogart

It is certified that error appears in the above-identified patent and that said Letters Patent is hereby corrected as shown below:

```
Column 1, line 23 "features" should be --fetuses--;
Column 1, line 31 "alphafetoprotein" should be --alpha-fetoprotein--;
Column 1, line 31 "wit" should be --with--;
Column 1, line 53 "of" should be --or--;
Column 1, line 58 "alph-HCG" should be --alpha-HCG--;
Column 2, line 23 "pesents" should be --presents--;
Column 2, line 24 "plcental" should be --placental--;
Column 3, line 27 "fetuses" should be --fetus--;
Column 3, line 56 "complete" should be --compete--;
Column 3, line 58 "on" should be --of--;
Column 4, line 9 "women" should be --woman--;
Column 4, line 25 "alpha HCG." should be --alpha-HCG.--;
Column 4, line 59 "densyl" should be --dansyl--;
Column 4, line 64 "allued" should be --alluded--;
Column 4, line 65 "levels" should be --labels--;
Column 5, line 9 "reproduction" should be --production--;
Column 7, line 63 "features" should be --fetuses--;
Column 9, line 4 "chainn" should be --chain--;
Column 10, claim 4, line 1 "wherei" should be --wherein--;
Column 10, claim 7, line 29 "surfaces, and" should be
    --surfaces thereon, and--.
```

Signed and Sealed this

Eleventh Day of December, 1990

Attest:

HARRY F. MANBECK, JR.

Attesting Officer

Commissioner of Patents and Trademarks